(12) United States Patent
Chen et al.

(10) Patent No.: US 8,383,881 B2
(45) Date of Patent: Feb. 26, 2013

(54) METHOD FOR PRODUCING POLYPLOID PLANTS OF ORCHIDS

(75) Inventors: Wen-Huei Chen, Taipei (TW); Yu-Lin Kao, Kaohsiung (TW); Ching-Yan Tang, Pingtung (TW)

(73) Assignee: National University of Kaohsiung, Kaohsiung (TW)

( * ) Notice: Subject to any disclaimer, the term of this patent is extended or adjusted under 35 U.S.C. 154(b) by 839 days.

(21) Appl. No.: 12/255,832

(22) Filed: Oct. 22, 2008

(65) Prior Publication Data

US 2009/0176227 A1 Jul. 9, 2009

(51) Int. Cl.
*A01H 1/00* (2006.01)
*A01H 1/02* (2006.01)

(52) U.S. Cl. .................................................. 800/268

(58) Field of Classification Search ............... 800/268, 800/276, 323; 435/441, 410, 420, 430, 430.1, 435/431
See application file for complete search history.

(56) References Cited

U.S. PATENT DOCUMENTS

| | | | | |
|---|---|---|---|---|
| 3,683,550 A * | 8/1972 | Corlett et al. | | 800/298 |
| 5,300,128 A * | 4/1994 | Matsunaga et al. | | 47/57.6 |
| 5,864,985 A * | 2/1999 | Zhou | | 47/62 N |
| 6,020,538 A * | 2/2000 | Han et al. | | 800/293 |
| 6,060,313 A * | 5/2000 | Zhou et al. | | 435/420 |
| 6,168,952 B1 * | 1/2001 | Oh et al. | | 435/430 |
| 6,218,184 B1 * | 4/2001 | Hasegawa et al. | | 435/431 |
| 7,049,489 B2 * | 5/2006 | Chen et al. | | 800/290 |
| 7,073,289 B2 * | 7/2006 | Chu et al. | | 47/58.1 R |

OTHER PUBLICATIONS

Sopalum et al. "Micropropagation of the Thai Orchid *Grammatophyllum speciosum* blume" Plant Cell Tiss Organ Cult (2010) 101:143-150.*
Teixeira da Sliva et al. Priming biotic factors for optimal protocorm-like body and callus induction in hybrid *Cymbidium* (Orchidaceae), and assessment of cytogenetic stability in regnerated plantlets. Plant Cell Tissue and Organ Culture (2006) 84: 135-144.*
Fukai et al. "Polysomaty is *Cymbidium*" HortScience 37(7) 1088-1091 2002.*
Miguel, Tilden P. and Kenneth W. Leonhardt "In vitro polyploid induction of orchids using oryzalin" Scientia Horticulturae 130 (2011) 314-319 Aug. 26, 2011.*
de Mello e Silva, Paulo Artur Konzen Xavier, Sidia Callegari-Jaques, Maria Helena Bodanese-Zanettini "Induction and Identification of Polyploids in *Cattleya intermedia* Lindl. (Orchidaceae) by in vitri Techniques" Ciencia Rural Santa Marie, v. 30 n. 1 pp. 105-111 2000.*
Chen, Wen Huei, Ching Yan Tang, Yu Lin Kao "Ploidy doubling by in vitro culture of excised protocorms or protocorm-like bodies in *Phalaenopsis* species" Plant Cell Tissue Organ Culture (2009) 98:229-238 Jun. 16, 2009.*

* cited by examiner

*Primary Examiner* — Wendy C Haas
(74) *Attorney, Agent, or Firm* — Alan Kamrath; Kamrath IP Lawfirm, P.A.

(57) ABSTRACT

A method for producing polyploid plants of orchids includes the steps of: providing a protocorm or protocom-like body (PLB) of an orchid, the protocorm or PLB having an upper portion with a growing point and a lower portion without any growing point; cutting the protocorm or PLB approximately at a point of half height to separate the upper portion; subculturing the lower portion of the protocorm or PLB in an inducing medium, and putting a cut surface of the lower portion of the protocorm or PLB to face upward so that one or more next-generation PLBs grow from the cut surface of the lower portion. The method characterized in using no antimicrotubule agent can simplify the entire process of orchid polyploidy breeding, and can be used in mass-production of the stable polyploid plants.

18 Claims, 3 Drawing Sheets

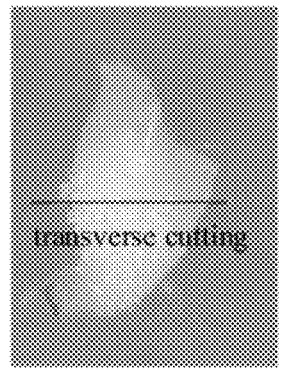 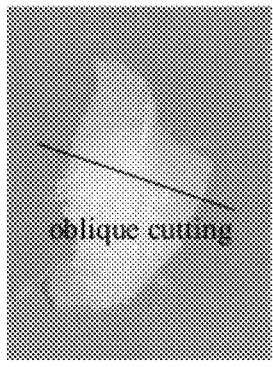 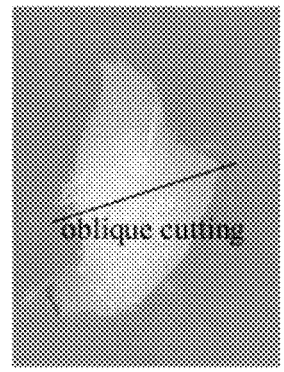
Fig. 1A     Fig. 1B     Fig. 1C
PLBs   Fig. 2

METHOD FOR PRODUCING POLYPLOID PLANTS OF ORCHIDS

BACKGROUND OF THE INVENTION

1. Field of the Invention

The present invention relates to a method for producing polyploid plants of orchids by physical cutting and plant tissue culture techniques. More particularly, the present invention relates to the method of utilizing plant tissue culture technique to induce endopolyploid cells, contained in a tissue culture material, to develop into polyploid plants, without using chemical agents (e.g. colchicine or other antimicrotubule agents).

2. Description of the Related Art

Today orchids, particularly *Phalaenopsis* (known as moth orchid), are one of the most important flower products for the markets in the United States of America and also in other countries. In order to maintain the superiority in the competitive market of *Phalaenopsis*, there is a need of developing new types of *Phalaenopsis* and improving native species of *Phalaenopsis* for the diversification of the product.

Most of the wild native *Phalaenopsis* species are diploids, and the tetraploid cultivars, however, are being successfully developed for the market in recent years. Therefore, the tetraploid *Phalaenopsis* hybrids have become popular in the market due to the fact that the tetraploid plants have bigger inflorescence and higher quality of their corolla and pedicels. On the other hand, only a few wild species of *Phalaenopsis* are tetraploid and are used in the breeding program to produce new hybrids or cultivars. Consequently, the genetic base of the cultivars of *Phalaenopsis* in the market nowadays is considerably inadequate, and the achievement of breeding for the new-type cultivars is limited. To obtain a superior new-type cultivar by integrating the desired characteristics (e.g. fragrance and color) of a wild species of *Phalaenopsis*, the orchid breeders attempted to develop new triploid cultivars by interspecific hybridization of the wild species of diploid and tetraploid. However, most of the triploid cultivars are highly sterile, and therefore cannot be further improved. Hence, there is a need of providing a simplified and effective breeding technique to obtain new polyploid cultivars of *Phalaenopsis*.

Currently, chemical agents are widely used for the chemical induction of chromosome doubling to produce ployploid plants in orchids. Several papers known in the arts demonstrate the usefulness of this approach for the above purpose. For example, the method of *Phalaenopsis* spp. disclosed by R. J. Griesbach (1981), Plant Cell Tissue Organ Culture, 1:103-107 and R. J. Griesbach (1985), The Journal of Heredity, 76:74-75; the method of *Cattleya intermedia* disclosed by P. A. K. X. de Mello e Silva et al. (2000), Ciência Rural, Santa Maria, 30:105-111; the method of *Cymbidium* Silky disclosed by M. S. Kim et al. (2003), Proceedings of NIOC2003 Nagoya, Japan, pp. 37-40; and the method of *Vanda* disclosed by H. Y. Nakasone (1961), Technical Bulletin, Hawaii Agricultural Experimental Station, U.S.A. are successful in utilizing the chemical agent of Colchicine to treat with the protocorms or protocorm-like bodies (PLBs) for the production of polyploid plants. Although these chemical-induction techniques can be successful in chromosome doubling, they can have disadvantages of operating in complicated procedure and problems of dealing with the toxicity of chemical agents which are unacceptable.

Some papers known in the arts further demonstrate the occurrence of the phenomenon of endoreduplication in several orchid cultivars. For example, endoreduplication of *Dendrobiutn* is disclosed by W. E. Jones and A. R. Kuehnle (1998), Lindleyana, 13:11-18; the chromosome endoreduplication phenomenon of *Phalaenopsis* is disclosed by S. Lin et al. (2001), J. Amer. Soc. Hort. Sci., 126:195-199; the chromosome endoreduplication phenomenon of *Spathoglottis* is disclosed by M. Yang and C. S. Loh (2004), BMC Cell Biology, 5:33; and the chromosome endoreduplication phenomenon of *Vanda* is disclosed by M. Yang and C. S. Loh (2003), New phytologist, 159:659-667. The phenomenon of endoreduplication means that the DNA contained in the nucleus is replicated and no cell division occurs, which results in endopolyploidy. In *Phalaenopsis* orchid, the phenomenon of endoreduplication is found commonly in various plant tissues (e.g. protocom, leaf, root and corolla), which is disclosed by H. C. Lee et al. (2003), Plant Science, 166:549-667, for example.

On the other hand, some other papers known in the arts further demonstrate that culturing of the leaf or root of *Phalaenopsis* in a proper medium could produce PLBs to regenerate the plants as disclosed by Hsu and Chen (2003), Journal Chinese Society Horticultural Science, 49:335-342 and T. W. Yam and M. A. Weatherhead (1991), Lindleyana, 6:151-153.

Some other papers known in the arts yet further point out that a method of physical cutting on the protocorms or protocorm-like bodies (PLBs) could induce multiplication of PLBs. For example, the method of physical cutting on the protocorm of *Phalaenopsis gigantea* and culturing it in a coconut-water and activated-charcoal-contained medium could achieve high-frequency multiplication of *Phalaenopsis gigantea* seedlings, which is disclosed by R. Murdad et al. (2006), Scientia Horticulturae, 111:73-79.

JP6046700 discloses a method for PLB proliferation of *Phalaenopsis*. The method requires cutting a tip slice of PLBs and culturing in a solid or liquid medium to obtain regeneration of PLBs. The regenerated PLBs could be subcultured and further proliferated by using the same method.

Each of the above-mentioned papers and Japanese patent is incorporated herein by reference for purposes including, but are not limited to, indicating the background of the present invention and illustrating the state of the art.

As is described in above-referenced papers and patent, the present invention provides a new and effective method of producing polyploid plants of orchids for the use in hybridization or induced mutation breeding.

SUMMARY OF THE INVENTION

The primary objective of this invention is to provide a method for producing polyploid plants of orchids by physical cutting and plant tissue culture techniques. The method includes the steps of:

(a). providing at least one protocorm or protocom-like body (PLB) of an orchid by plant tissue culture technique under sterile condition, the protocorm or PLB having a predetermined height of 2-8 mm and having an upper portion with a growing point and a lower portion without any growing point, the lower portion located beneath the upper portion;

(b). cutting the protocorm or PLB approximately at a point of half height to separate the upper portion and the lower portion such that the upper portion has a first cut surface and the lower portion has a second cut surface correspondingly;

(c). subculturing the lower portion of the protocorm or PLB in an inducing medium, and putting the second cut surface of the lower portion of the protocorm or PLB to face upward so that one or more next-generation PLBs grow from the second cut surface of the lower portion;

(d). cutting off at least one of the next-generation PLBs from the second cut surface of the lower portion when growing to a preferred height (2-8 mm, for example);

(e). repeating the steps (b) through (d) one or more times if necessary;

(f). cultivating the next-generation PLBs obtained from the step (d) or (e) in a regenerating medium so as to differentiate the next-generation PLBs into plantlets; and (g). processing a chromosome ploidy analysis to identify the ploidy level of the plantlets.

The method of the present invention is characterized in producing polyploid plants from the endopolyploid cells in tissue culture materials by plant tissue culture techniques without using any chemical agent, such as colchicine or other antimicrotubule agents. Advantageously, the method can produce a large amount of the polyploid plants of orchids and can simplify the entire process of orchid polyploidy breeding.

Further scope of the applicability of the present invention will become apparent from the detailed description given hereinafter. However, it should be understood that the detailed description and specific examples, while indicating preferred embodiments of the invention, are given by way of illustration only, since various modifications will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIGS. 1A-1C are images of transverse cutting and oblique cutting on protocorms processed in a method for producing polyploid plants of orchids in accordance with the preferred embodiment of the present invention;

FIG. 2 is an image of protocorms of diploid of *Phal. aphrodite* subsp. *formosana* being cut and cultured for 2-3 months in the method in accordance with the preferred embodiment of the present invention;

DETAILED DESCRIPTION OF THE INVENTION

Figure 3A:
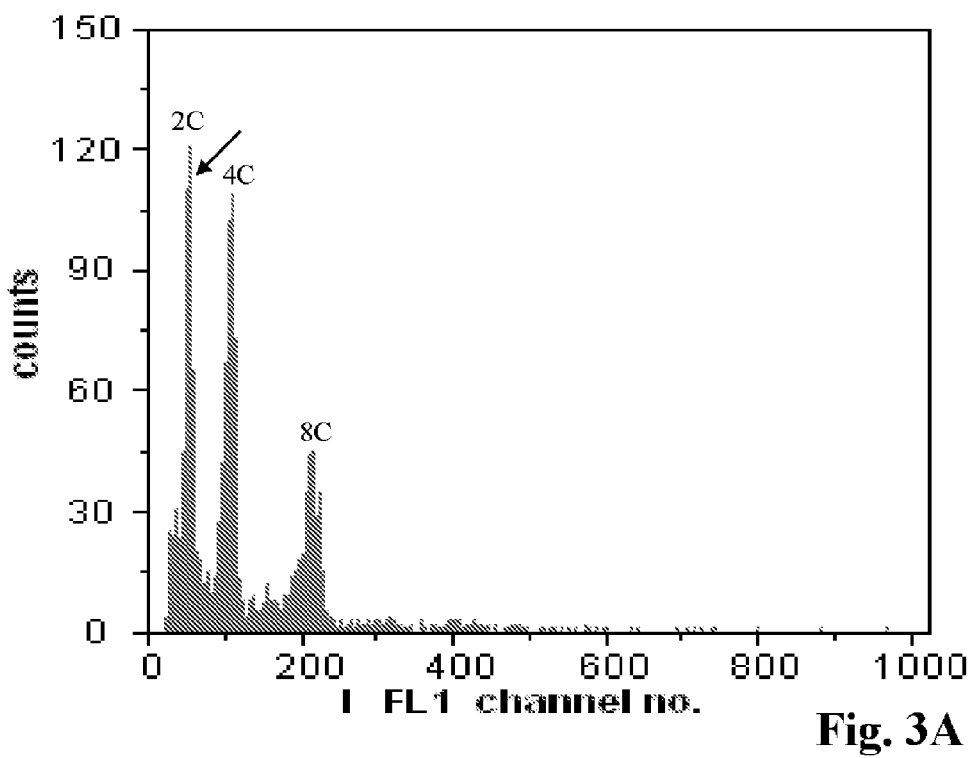
FIG. 3A is a flow cytometric histogram showing DNA content (i.e. c-value) of leaf cell nuclei of diploid of a regenerated plant of the third-generation PLB produced by the method in accordance with the preferred embodiment of the present invention, wherein C-value represents the multiple of the basic DNA content.

Before describing the invention in greater detail, the word "comprise" or variations such as "comprises" or "comprising," will be understood to imply the inclusion of a stated integer or group of integers but not the exclusion of any other integer or group of integers.

It should be appreciated that the scope of the present invention shall not be limited to any relevant prior art, incorporated herein by reference, to the present invention.

Throughout the specification, unless the context requires otherwise, the technical terms, as used herein, have the same meaning as one of ordinary skill commonly known in the art.

Currently, colchicine is generally used to treat protocorms or protocom-like bodies (PLBs) of an orchid for inducing ployploid plants of orchids. Although the chemical-induction technique can be successful in chromosome doubling, it can have disadvantages of operating in complicated procedure and problems of dealing with the toxicity of chemical agents which are unacceptable.

The method for producing polyploid plants of orchids in accordance with the present invention includes physical cutting the protocorms or protocom-like bodies (PLBs) of orchids at a predetermined position thereof, and culturing the protocorms or PLBs in a medium to induce a new next-generation PLBs by plant tissue culture techniques. When growing up to a predetermined size, the new next-generation PLBs are cut off and processed by further cutting and culturing them so as to increase the number of PLBs and to have a high frequency of polyploidy. Subsequently, the new next-generation PLBs are cultivated in a regenerating medium so as to differentiate the next-generation PLBs into plantlets. Furthermore, a flow cytometer is used to process a chromosome ploidy analysis in identifying the ploidy level of the plantlets.

In a preferred embodiment, the protocorm or PLB has a physical cutting position (i.e. middle point or half height position) on which next-generation PLBs have a higher possibility of being induced and differentiating into polyploid plants. In addition to this, chromosome duplication of the polyploid plants is highly stable and may not be specifically deteriorated when increasing the culturing time.

As has been described above, the method for producing polyploid plants of orchids in accordance with a preferred embodiment of the present invention utilizes physical cutting and plant tissue culture techniques to activate endopolyploid cells, contained in a tissue culture material, to develop and become polyploid plants, without the need of using chemical agents (e.g. colchicine or other antimicrotubule agents). The method of the preferred embodiment of the present invention includes the steps of:

(a). providing at least one protocorm or protocom-like body (PLB) of an orchid by plant tissue culture technique under sterile condition, the protocorm or PLB having a height of 2-8 mm and having an upper portion with a growing point and a lower portion without any growing point, the lower portion located beneath the upper portion;

(b). cutting the protocorm or PLB approximately at a point of half height to separate the upper portion and the lower portion such that the upper portion has a first cut surface and the lower portion has a second cut surface correspondingly;

(c). subculturing the lower portion of the protocorm or PLB in an inducing medium, and putting the second cut surface of the lower portion of the protocorm or PLB to face upward so that one or more next-generation PLBs grow from the second cut surface of the lower portion;

(d). cutting off at least one of the next-generation PLBs from the second cut surface of the lower portion when growing to a height of 2-8 mm;

(e). repeating the steps (b) through (d) one or more times if necessary;

(f). cultivating the next-generation PLBs obtained from the step (d) or (e) in a regenerating medium so as to differentiate the next-generation PLBs into plantlets; and (g). processing a chromosome ploidy analysis to identify the ploidy level of the plantlets.

Throughout the specification, the terms "plant tissue culture technique," "plant tissue culture," or "tissue culture" may be interchanged with one another. The term "plant tissue culture technique," as used herein, means that a series of operational steps is applied to supply plant organs, plant tissues or plant cells with growth conditions (e.g. light, temperature, nutrient, plant hormones or plant growth regulators etc.) under sterile condition to multiply or regenerate the plant organs or the whole plants.

The orchid plants applied in the preferred embodiment of the present invention, but are not limited to, include: wild species, cultivors or hybrids of *Phalaenopsis, Doritis, Dendroblunt Spathoglottis*, and *Vanda*. Preferably, the orchid plants are selected from wild species, cultivors or hybrids of *Phalaenopsis* . More preferably, the orchid plants are selected from *Phal. aphrodite* subsp. *formosana, Phal. bellina, Phal. amabilis, Phal. aphrodite, Phal. arnboinensis, Phal. cornucervi, Phal. equestris, Phal. fasciata, Phal. gigantea, Phal. hieroglyphica, Phal. inscriptiosinensis, Phal. lueddemanniana, Phal. lindenii, Phal. lobbii, Phal. manni, Phal. mariae, Phal. micholitzii, Phal. parishii, Phal. philippinensis, Phal. pulchra, Phal. sanderiana, Phal. schilleriana, Phal. stuartiana, Phal. venosa, Phal. violacea, Phal. wilsonii* and *Doritis pulcherrima*.

In a preferred embodiment, the orchid plants are selected from *Phal. aphrodite* subsp. *formosana*. In another preferred embodiment, the orchid plants are selected from *Phal. bellina*.

The first step (a) of the method in accordance with the present invention is: providing a protocorm selected from a germinated seed of an orchid or a protocom-like body (PLB) grown from a plant tissue of an orchid plant, such as a protocorm, root, leaf, stalk, pedicel axillary bud, pedicel terminal bud, ovary and combinations thereof. In a preferred embodiment, provided in first step (a) is the protocorm selected from a seed of an orchid plant.

In the preferred embodiment, the protocorm or PLB provided in first step (a) must be sized within a range of predetermined heights, and is cut in second step (b). Preferably, the height of the protocorm or PLB ranges from 2 mm to 8 mm. More preferably, the height of the protocorm or PLB ranges from 3 mm to 5 mm.

In the preferred embodiment, cutting the protocorm or PLB is transverse cutting in second step (b). In an alternative embodiment, cutting the protocorm or PLB is oblique cutting.

In third step (c), the inducing medium applied in the present invention is selected from a solid medium or a liquid medium. The ingredients of the solid medium may be inorganic salts (e.g. MS basal salts disclosed by Murashige T. and Skoog F. (1962), Physiol. Plant, 15:473-497 and Chu (1988), Seeding and Tissue Culture of *Phalaenopsis* , Western Orchid Press, Taiwan, or Hyponex No. 1), saccharides (e.g. sucrose), organic supplements (e,g, tryptone or peptone), gelling agent (e.g. agar) and plant growth regulators. Preferably, the plant growth regulators are selected from the group consisting of: auxins (e.g. naphthaleneacetic acid, NAA), cytokinins (e.g. $N^6$-benzyladenine, BA) and combinations thereof. Alternatively, the plant growth regulators can be substituted by natural additives. The natural additives applied in the present invention include, but are not limit to, homogenized potato, homogenized banana and coconut water, etc. The ingredients of the liquid medium applicable to the present invention are the same with those of the solid medium, and no gelling agent is added in the liquid medium.

In the preferred embodiment, the inducing medium can be prepared as disclosed by Chu (1988). In another preferred embodiment, the growth of PLB can be induced by T2 inducing medium in third step (c).

In the preferred embodiment, in fifth step (e), the next-generation PLB obtained from fourth step (d) is repeated in processing twice via second step (b) to fourth step (d).

In the preferred embodiment, in sixth step (f), the regenerating medium is suitable for inducing and differentiating the next-generation PLB into orchid plantlets. The regenerating medium is selected from a solid medium or a liquid medium. In a preferred embodiment, the solid medium is selected from inorganic salts (e.g. MS basal salts and Hyponex No. 1), saccharides, organic supplements (e.g. tryptone or peptone), gelling agent (e.g. agar) and plant growth regulators. Preferably, the plant growth regulators are selected from the groups consisting of: auxins, cytokinins and combinations thereof. In general, the amount of the growth regulators in the regenerating medium used in the present invention is less than that of the inducing medium. Alternatively, the plant growth regulators can be substituted by natural additives. The natural additives applied in the present invention contain, but are not limited to, homogenized potato, homogenized banana and/or coconut water, etc. The ingredients of the liquid medium applicable to the present invention are the same with those of the solid medium, and no gelling agent is added in the liquid medium.

In a preferred embodiment, the differentitation of PLB can be induced in sixth step (f) by T2 regenerating medium which consists of the following ingredients: Hyponex No. 1 (3.5 g/L), citric acid (0.1 g/L), tryptone (1.0 g/L), sucrose (20 g/L), potato (20 g/L), banana (20 g/L), charcoal (1.0 g/L) and agar (8.5 g/L) with pH adjusted to 5.5.

In seventh step (g), methods of chromosome ploidy analysis include, but are not limited to, microscopic method, morphological identification method and flow cytometric analysis method. In a preferred embodiment, a flow cytometer is used to process a chromosome ploidy analysis in identifying the ploidy level of the plantlets.

As has been described above, the inducing method for regenerating plants from PLBs of orchids in accordance with the present invention is successful in achieving a higher frequency of chromosome doubling, and in trending an increase of frequency of chromosome doubling according to the PLB generations (i.e. the number of physical cutting). Advantageously, the polyploid plants obtained from the method of the present invention is highly stable and may not be specifically deteriorated when increasing the culturing time such that the method of the present invention is suitable for orchid polyploidy breeding including hybridization, induced mutation, and new breed developing and improving.

The following experimental examples are provided to illustrate the present invention. Experiments were conducted to demonstrate the feasibility of various embodiments of the present invention.

Experiment 1

This experiment is conducted to demonstrate the effect of cutting the protocorm or PLB upon chromosome doubling of orchid regenerated plants.

Experimental Material:

1. Preparing a Seeding Medium:

In this experiment, the seeding medium is selected from MSp medium whose ingredients include MS salt (1.1 g/L), tryptone (1.0 g/L), sucrose (20 g/L), potato (8.5 g/L) and agar (8.5 g/L). Preferably, the medium having a pH value of 5.8 is sterilized in an autoclave at 121° C. for 15 minutes.

2. Preparing a PLB-Inducing Medium and a Regenerating Medium:

In this experiment, the PLB-inducing medium and the regenerating medium are selected from T2 medium whose ingredients include Hyponex No. 1 (3.5 g/L), citric acid (0.1 g/L), tryptone (1.0 g/L), sucrose (20 g/L), potato (20 g/L), banana (20 g/L), charcoal (1.0 g/L) and agar (8.5 g/L). Preferably, the medium having a pH value of 5.5 and is sterilized in an autoclave at 121° C. for 15 minutes.

3. Protocorm Sources:

(1). Preparing protocorms of diploid *Phal. aphrodite* subsp. *formosana*, triploid *Phal. aphrodite* subsp. *formosana* and tetraploid *Phal. aphrodite* subsp. *formosana*.

Firstly, plants of diploid and tetraploid *Phal. aphrodite* subsp. *formosana* available in Taiwan are used for self-pollination to obtain diploid and tetraploid seeds thereof. Furthermore, these diploid and tetraploid plants of *Phal. aphrodite* subsp. *formosana* are crossed with each other to obtain triploid seeds thereof.

Subsequently, 0.05 g seeds of diploid, triploid and tetraploid of *Phal. aphrodite* subsp. *formosana* are processed for surface disinfection by 0.3% sodium hypochloride solution for 5 minutes, and then are washed with sterilized water three times under aseptic condition. The seeds are sown in the MSp medium, and are cultured in a culture room where the temperature is within 25±2° C., the illuminance is less than 1,000 1×, and the illuminating time is 16 hrs per day. After culturing for 3 months, protocorms are grown to have a height of 3-4 mm.

(2). Protocorms of diploid *Phalaenopsis f* used in this experiment are available from the Four Seasons Orchids in Kaohsiung, Taiwan, and has a height of 4-5 mm.

Method of Experiment:

A. Inducing Growth of Protocorm-Like-Bodies (PLBs) and Plant Regeneration:

One hundred protocorms of each of diploid, triploid and tetraploid of *Phal. aphrodite* subsp. *formosana* and diploid of *Phalaenopsis bellina* are selected and subcultured for inducing PLBs in the following experiment. Firstly, as best shown in FIGS. 1A to 1C, a scalpel (handle No. 3 and blade No. 11) is used to cut the protocorm approximately at a point of half height by transverse cutting (identified as reference line in FIG. 1A) or oblique cutting (identified as reference lines in FIGS. 1B and 1C). Accordingly, the upper portion of the protocorm having a growing point is cut off and removed such that the lower portion of the protocorm without any growing point is obtained and formed with a cut surface. The lower portion of the protocorm with the cut surface facing upward is subcultured in a T2 inducing medium provided in a Petri dish which has a diameter of 9 cm. Preferably, each of the Petri dishes accommodates about 20 to 25 lower portions of the protocorms. Subsequently, the lower portions of the protocorms contained in the Petri dish are placed in a culture room where the temperature is within 25±2° C., the illuminance is less than 1,000 1×, and the illuminating time is 16 hrs per day. After culturing for one month, first-generation PLBs are grown from the cut surface of the lower portion of the protocorm. After culturing for 2 to 3 months, the first-generation PLBs are grown up to a height of 3-4 mm, as best shown in FIG. 2. The first-generation PLBs are then cut off from the lower portions of the protocorms. In order to produce second-generation PLBs, one hundred first-generation PLBs are selected and repeatedly processed in the above-mentioned experimental steps. Furthermore, one hundred second-generation PLBs are selected and repeatedly processed in the above-mentioned experimental steps to produce third-generation PLBs.

For each generation, another 100-150 protocorms or PLBs obtained by induction of each of diploid, triploid and tetraploid of *Phal. aphrodite* subsp. *formosana*, and of diploid *Phalaenopsis bellina* are selected and induced in the following experimental steps so as to regenerate the plants. Firstly, the protocorms or PLBs are subcultured in a T2 inducing medium provided in a Petri dish. Subsequently, the Petri dishes are placed in a culture room where the temperature is within 25±2° C. the illuminance is 2,000 1×, and the illuminating time is 16 hrs per day. After culturing for 3 to 5 months, regenerated plantlets grown with 3-4 leaves are obtained for further studies.

B. Extraction and Staining of Leaf Cell Nuclei:

In this experiment, a Cystain UV precise P kit manufactured by Partec, Münster, Germany is used in extraction and staining of leaf cell nuclei, and the procedure of extraction and staining is processed on an ice bath filled with ice fragments. Firstly, 30-40 mg of newly developed leaves of the regenerated plants previously obtained in the experiment in accordance with the present invention (as best shown in FIGS. 1A-1C and 2, and as disclosed in the section "A" above) are cut off and placed in a flat-bottomed glass Petri dish (having a diameter of 5.5 cm), and 100 μl of extraction buffer is added in the Petri dish. Subsequently, the newly developed leaves are cut into fragments less than 1 mm by a double-sided razor blade, and are mixed with 400 μl of DAPI staining buffer in the Petri dish. The leaf fragment mixtures containing leaf cell nuclei are filtered through a filter having a mesh size of 30 μm. Accordingly, the filtrates are used for chromosome ploidy analysis in the subsequent procedure.

Additionally, seedling leaf tissues of diploid *Phal. aphrodite* subsp. *formosana* which is known to have 2.8 pg/2 C DNA content are selected as reference and processed in the same extraction and staining procedures as has been previously described above. Accordingly, filtrates obtained in these known samples serve as a reference for the adjustment of the 'gain' value in a flow cytometer.

C. Identifying Chromosome Ploidy Level of Regenerated Plants:

A Partec PA-I flow cytometer (manufactured by Partec, Münster, Germany) is used to analyze a DNA content of leaf samples obtained in the experiment in accordance with the present invention (as disclosed in the section "B" above), wherein a channel number of the $G_0/G_1$ peak represents the DNA content of the samples. Prior to each measuring procedure, a reference extracting solution prepared in the experiment in accordance with the present invention (as disclosed in the section "B" above) is used to adjust the 'gain' value of the flow cytometer so that the channel number of the $G_0/G_1$ peak of the reference solution is set at 50. Under this condition, the channel number of $G_0/G_1$ peak measured for the leaf sample of the plantlet developed directly from the diploid protocom of a particular species represents the datum value so as to identify the ploidy levels of the regenerated plants of the same *Phalaenopsis* species.

Figure 3B:
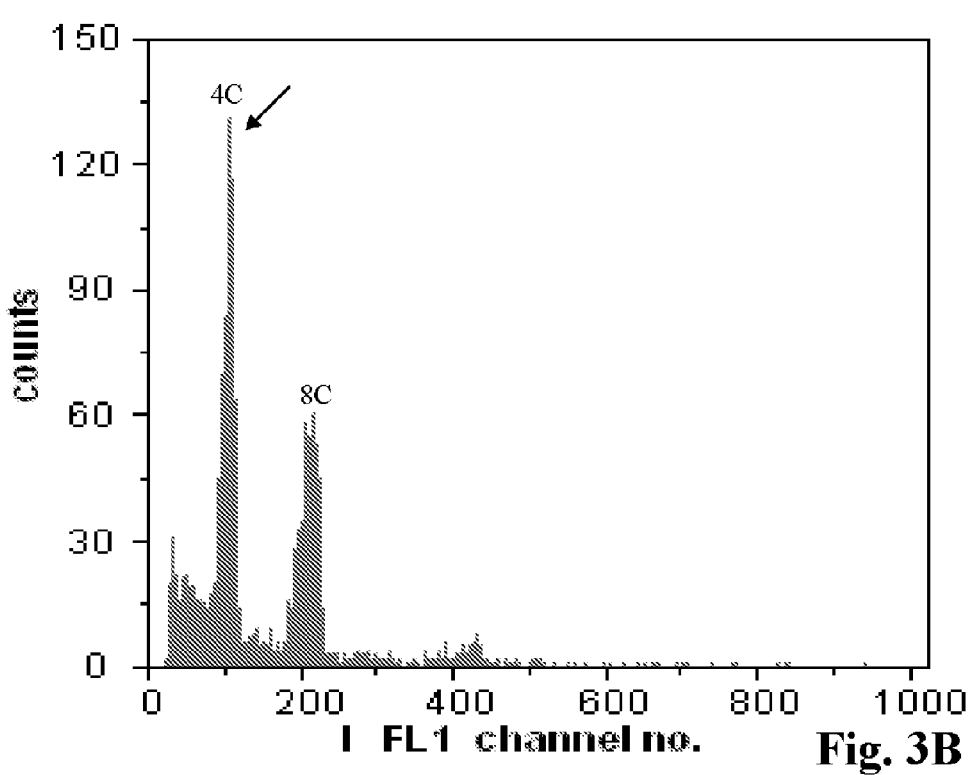
FIG. 3B is a flow cytometric histogram showing DNA content (i.e. c-value) of leaf cell nuclei of tetraploid of a regenerated plant of the third-generation PLB produced by the method in accordance with the preferred embodiment of the present invention.

The rules of identifying the occurrence of chromosome doubling or the ploidy levels of the regenerated plants are as follows: if the channel number of $G_0/G_1$ peak position measured for the regenerated plant is the same or closely the same with the datum value of a particular species, this means that the DNA content of the leaf cell nuclei of the regenerated plant remains in the same ploidy level as diploid (FIG. 3A); and if the channel number of $G_0/G_1$ peak position measured for the regenerated plant has doubled or quadrupled that of the datum value, this means that the DNA content of the leaf cell nuclei or the chromosome of the regenerated plant is doubled once or twice, and the regenerated plant can be identified as a polyploid plant or a plant having chromosome doubled (FIG. 3B).

The identifying result can be represented by a frequency of chromosome doubling which can be calculated in the following equation:

$$Y=(P/N)\times 100$$

where Y is frequency of chromosome doubling (%),

P is the number of identified polyploid plants or plants having chromosome doubled, and N is the total number of regenerated plants studied.

Result:

The resulting histograms of identifying the ploidy level of regenerated plants from different generations as given by the flow cytometer are similar. Hence, the result of the third-generation PLB of diploid and tetraploid of *Phal. aphrodite* subsp. *formosana* diploid obtained in the experiment in accordance with the present invention (as disclosed in the section "A" above) are given for illustration only. Referring now to FIG. 3A, the channel number of the $G_0/G_1$ peak position of a leaf sample from the third-generation plantlet of the *Phal. aphrodite* subsp. *formosana* is 51.4 (indicated by the arrow) which is closely approaching the datum value of diploid *Phal. aphrodite* subsp. *formosana* which is set at the channel number 50. Accordingly, this third-generation plantlet is identified as diploid. Referring now to FIG. 3B, the channel number of the $G_0/G_1$ peak position of a leaf sample from another third-generation plantlet of the diploid *Phal. aphrodite* subsp. *formosana* is 104.3 (indicated by the arrow) which closely double the datum value of diploid *Phal. aphrodite* subsp. *formosana*. Accordingly, this third-generation plantlet is identified as tetraploid.

Figure 4:
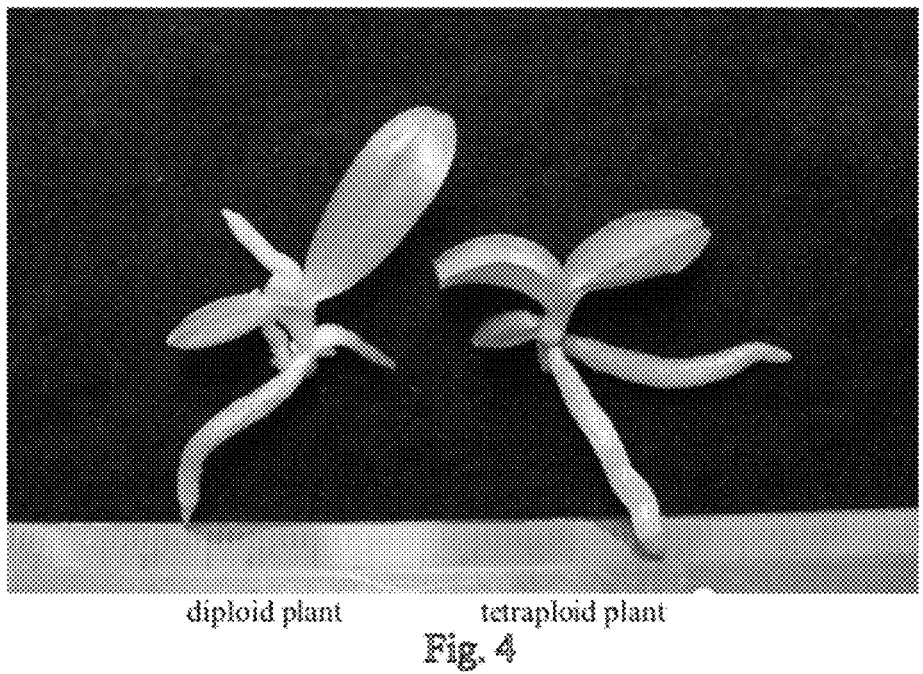
FIG. 4 is an image of a diploid plant (left side) and a tetraploid plant (right side) produced by the method in accordance with the preferred embodiment of the present invention.

Referring to FIG. 4, the identified diploid plant (left side) and the identified tetraploid plant (right side) produced by the method in accordance with the present invention are shown. In FIG. 4, the tetraploid plant has a root and leaf thickness thicker than those of the diploid plant, and has a leaf color deeper than that of the diploid plant.

Table 1 shows the frequencies of chromosome doubling of diploid, triploid and tetraploid of *Phal. aphrodite* subsp. *formosana* and diploid of *Phalaenopsis bellina* produced by the method in accordance with the present invention. As can be seen in Table 1, the frequencies of chromosome doubling are different in different generations of regenerated plants of the diploid, the triploid and the tetraploid of *Phal. aphrodite* subsp. *formosana* and the diploid of *Phalaenopsis bellina*. The average frequency of the protocom generation is only 0.7%, but the average frequencies of first to third cutting generations are 11.4%, 31.4% and 44.0%, respectively. It is found that the different species or different lines of the same species having different ploidy levels processed by the method of the present invention can be successful in achieving a higher degree of frequency of chromosome doubling. The frequency of chromosome doubling can tend to increase as its generation (i.e. the number of cutting) increases.

TABLE 1

Frequencies of chromosome doubling of plantlets of different generations obtained from diploid, triploid and tetraploid of *Phal. aphrodite* subsp. *formosana* and diploid of *Phalaenopsis bellina* by the method in accordance with the present invention.

| Phalaenopsis lines/ species | Frequency of chromosome doubling (%) | | | |
| --- | --- | --- | --- | --- |
| | Protocorm generation | First generation | Second generation | Third generation |
| Diploid *Phal. aphrodite* subsp. *Formosana* | 1.8 | 25.4 | 61.6 | 66.2 |
| Triploid *Phal. aphrodite* subsp. *formosana* | 0.8 | 8.6 | 33.2 | 37.2 |
| Tetraploid *Phal. aphrodite* subsp. *formosana* | 0 | 3.7 | 10.6 | 16.0 |

TABLE 1-continued

Frequencies of chromosome doubling of plantlets of different generations obtained from diploid, triploid and tetraploid of *Phal. aphrodite* subsp. *formosana* and diploid of *Phalaenopsis bellina* by the method in accordance with the present invention.

| Phalaenopsis lines/ species | Frequency of chromosome doubling (%) | | | |
| --- | --- | --- | --- | --- |
| | Protocorm generation | First generation | Second generation | Third generation |
| Diploid *Phalaenopsis bellina* | 0 | 7.7 | 20.1 | 56.7 |
| Average frequency | 0.7 | 11.4 | 31.4 | 44.0 |

Experiment 2

This experiment is conducted to evaluate the stability of chromosomes in the induced polyploid plants during cultivation. Any change of the chromosome ploidy levels during the cultivation of the induced tetraploid plants of *Phal. aphrodite* subsp. *formosana* and *Phalaenopsis bellina* (as identified in the section "C" of the experiment 1 above) obtained from the diploid *Phal. aphrodite* subsp. *formosana* and *Phalaenopsis bellina* (as disclosed in the section "A" of the experiment 1 above) are used as an indicator of the stability level.

Method of Experiment:

The tetraploid plantlets of *Phal. aphrodite* subsp. *formosana* and *Phalaenopsis bellina* (as identified in the section "C" of Experiment 1 above) are transplanted to plastic pots (with a diameter of 1.7 inches) which are provided with a potting medium containing peat moss. The tetraploids of *Phal. aphrodite* subsp. *formosana* and *Phalaenopsis bellina* are cultured in a culture room where the temperature is within 27±2° C., the illuminance is 3,000 1x, and the illuminating time is 16 hrs per day. After culturing for 3-5 months, newly developed leaves are grown from tetraploids of *Phal. aphrodite* subsp. *formosana* and *Phalaenopsis bellina*. Subsequently, the newly developed leaves of tetraploids of *Phal. aphrodite* subsp. *formosana* and *Phalaenopsis bellina* are selected to process the procedures of extraction and staining of leaf cell nuclei (as disclosed in the section "B" of Experiment 1 above) and identifying chromosome ploidy levels of regenerated plants (as disclosed in the section "C" of Experiment 1 above). The results in great detail are set forth in Table 2.

Result:

Table 2 shows the frequencies of the ploidy levels of tetraploid plants of *Phal. aphrodite* subsp. *formosana* and *Phalaenopsis bellina* produced by the method in accordance with the present invention. These tetraploid plants are grown for 3-5 months in the culture room. As can be seen in Table 2, after culturing 3-5 months, the frequencies of these plants having the same ploidy level as tetraploids of regenerated plants of *Phal. aphrodite* subsp. *formosana* and *Phalaenopsis bellina* are 96.6% and 96.3% respectively. It can be found that the ploidy level of most of the polyploid plants produced by the method in accordance with the present invention will not change as its culturing time extends to 3-5 months, such that the polyploid plants are highly stable.

TABLE 2

The change of the ploidy levels after cultivation for 3-5 months of the tetraploid plantlets of *Phal. aphrodite* subsp. *formosana* and *Phalaenopsis bellina* of regenerated plants obtained by the method in accordance with the present invention.

| *Phalaenopsis* species | Numbers of tetraploid plants studied | Frequencies of plants having different ploidy levels | | |
|---|---|---|---|---|
| | | 2× | 4× | 8× |
| Teraploid *Phal. aphrodite* subsp. *formosana* | 117 | 0.9 | 96.6 | 2.5 |
| Teraploid *Phalaenopsis bellina* | 27 | 3.7 | 96.3 | 0 |

Although the invention has been described in detail with reference to its presently preferred embodiments, it will be understood by one of ordinary skill in the art that various modifications can be made without departing from the spirit and the scope of the invention, as set forth M the appended claims.

What is claimed is:

1. A method for producing polyploid plants of orchids comprising:
   (a). providing at least one protocorm or protocom-like body (PLB) of an orchid, with the protocorm or PLB having an upper portion with a growing point and a lower portion without any growing point, with the lower portion having a plurality of polyploidy cells;
   (b). cutting the protocorm or PLB at a predetermined point to separate the upper portion and the lower portion, wherein the upper portion has a first cut surface and the lower portion has a second cut surface, and removing the upper portion having the growing point;
   (c). subculturing the lower portion of the protocorm or PLB without any growing point in an inducing medium to induce the growth of the plurality of polypoidy cells, wherein one or more next-generation PLBs grow from the second cut surface of the lower portion;
   (d). cutting off at least one of the one or more next-generation PLBs from the second cut surface of the lower portion;
   (e). repeating (b) through (d) one or more times; and
   (f). subculturing the next-generation PLBs obtained from (d) or (e) in a regenerating medium to differentiate the next-generation PLBs into plantlets and identifying the plantlets of the next-generation PLBs.

2. The method for producing polyploid plants of orchids as defined in claim 1, wherein the at least one protocorm or PLB has a height of 2-8 mm.

3. The method for producing polyploid plants of orchids as defined in claim 1, wherein cutting the protocorm or PLB is at the predetermined point of a half height of the at least one protocorm or PLB.

4. The method for producing polyploid plants of orchids as defined in claim 1, further comprising: putting the second cut surface of the lower portion of the protocorm or PLB to face upward before subculturing.

5. The method for producing polyploid plants of orchids as defined in claim 1, wherein the orchids include: wild species or hybrid of *Phalaenopsis, Doritis, Dendrobium, Spathoglottis*, and *Vanda*.

6. The method for producing polyploid plants of orchids as defined in claim 1, wherein the orchids are selected from *PhaL aphrodite* subsp. *formosana, Phal. bellina, Phal. amabilis, Phal. aphrodite, Phal. amboinensis, Phal. cornu-cervi, Phal. equestris, Phal. fasciata, Phal. gigantea, Phal. hieroglyphica, Phal. inscriptiosinensis, Phal. lueddemanniana, Phal. lindenii, Phal. lobbii, Phal. mannii, Phal. mariae, Phal. micholitzii, Phal. parishii, Phal. philippinensis, Phal. pulchra, Phal. sanderiana, Phal. schilleriana, Phal. stuartiana, Phal. venosa, Phal. violacea, PhaL wilsonii* and *Doritis pulcherrima*.

7. The method for producing polyploid plants of orchids as defined in claim 1, wherein the at least one protocorm is selected from a germinated orchid seed.

8. The method for producing polyploid plants of orchids as defined in claim 1, wherein the PLB grown from a plant tissue selected from a protocorm, a root, a leaf, a stalk, a pedicel axillary bud, a pedicel terminal bud, an ovary and combinations thereof.

9. The method for producing polyploid plants of orchids as defined in claim 1, wherein cutting the protocorm or PLB comprises transverse cutting or oblique cutting.

10. The method for producing polyploid plants of orchids as defined in claim 1, wherein the inducing medium includes inorganic salts, saccharides, organic supplements, and plant hormones or plant growth regulators.

11. The method for producing polyploid plants of orchids as defined in claim 10, wherein the plant hormones or plant growth regulators are selected from a group consisting of: auxins, cytokinins and a combination thereof.

12. The method for producing polyploid plants of orchids as defined in claim 1, wherein the inducing medium contains homogenized potato, homogenized banana and/or coconut water.

13. The method for producing polyploid plants of orchids as defined in claim 1, wherein the regenerating medium includes inorganic salts, saccharides, organic supplements, and plant hormones or plant growth regulators.

14. The method for producing polyploid plants of orchids as defined in claim 13, wherein the plant hormones or plant growth regulators are selected from a group consisting of: auxins, cytokinins and a combination thereof; and wherein the quantity of plant hormones or plant growth regulators is less than that of the PLB inducing medium.

15. The method for producing polyploid plants of orchids as defined in claim 1, wherein the regenerating medium contains homogenized potato and homogenized banana.

16. The method for producing polyploid plants of orchids as defined in claim 1, further comprising: (g). processing a DNA ploidy analysis to identify a ploidy level of the plantlets and to isolate the plantlets of the next-generation PLBs.

17. The method for producing polyploid plants of orchids as defined in claim 16, further comprising using a flow cytometer to process the DNA ploidy analysis.

18. The method for producing polyploid plants of orchids as defined in claim 1, wherein inducing the growth of the plurality of polypoidy cells occurs in absence of antimicrotubule agents.

\* \* \* \* \*